United States Patent
Sarstedt

(10) Patent No.: US 8,333,711 B2
(45) Date of Patent: Dec. 18, 2012

(54) BLOOD-DRAWING DEVICE, IN PARTICULAR FOR INFANTS AND SMALL CHILDREN OR SMALL ANIMALS

(75) Inventor: Walter Sarstedt, Numbrecht (DE)

(73) Assignee: Sarstedt AG & Co., Nuembrecht (DE)

( * ) Notice: Subject to any disclaimer, the term of this patent is extended or adjusted under 35 U.S.C. 154(b) by 1511 days.

(21) Appl. No.: 11/587,836

(22) PCT Filed: Apr. 21, 2005

(86) PCT No.: PCT/DE2005/000737
§ 371 (c)(1),
(2), (4) Date: Sep. 4, 2007

(87) PCT Pub. No.: WO2005/104947
PCT Pub. Date: Nov. 10, 2005

(65) Prior Publication Data
US 2008/0033464 A1    Feb. 7, 2008

(30) Foreign Application Priority Data
Apr. 30, 2004 (DE) .......................... 10 2004 021 741

(51) Int. Cl.
*A61B 5/00* (2006.01)
(52) U.S. Cl. ........................................ 600/583
(58) Field of Classification Search .......... 600/573–584; 606/181–183; 604/190, 266
See application file for complete search history.

(56) References Cited

U.S. PATENT DOCUMENTS

| 4,595,021 A | 6/1986 | Shimizu et al. ............... 128/760 |
| 4,653,511 A | 3/1987 | Goch et al. .................... 128/763 |
| 4,703,763 A | 11/1987 | McAlister et al. ............ 128/765 |
| 5,165,419 A | 11/1992 | Sarsted ........................ 128/763 |

FOREIGN PATENT DOCUMENTS

DE     10060302     6/2002

*Primary Examiner* — Brian Szmal
(74) *Attorney, Agent, or Firm* — Andrew Wilford

(57) ABSTRACT

The invention relates to a blood taking device (1), in particular, for newborn babies and small children or small animals, comprising a blood taking vessel (2), provided on the front end thereof with a cannula (5) with a sharpened tip (4), whereby a porous, gas-permeable limiting element (8) which automatically stops the flow of taken blood, is arranged by pressing in the blood taking vessel (2) in a defined position. The rear end of the blood taking vessel (2) is sealed by a plug (11) which may be temporarily opened for taking blood (11), which dispenses the taken blood by means of a stroke running in a sealed manner in the blood taking vessel (2), which empties under pressure at least a part amount of the blood retained before the limiting element (8).

3 Claims, 1 Drawing Sheet

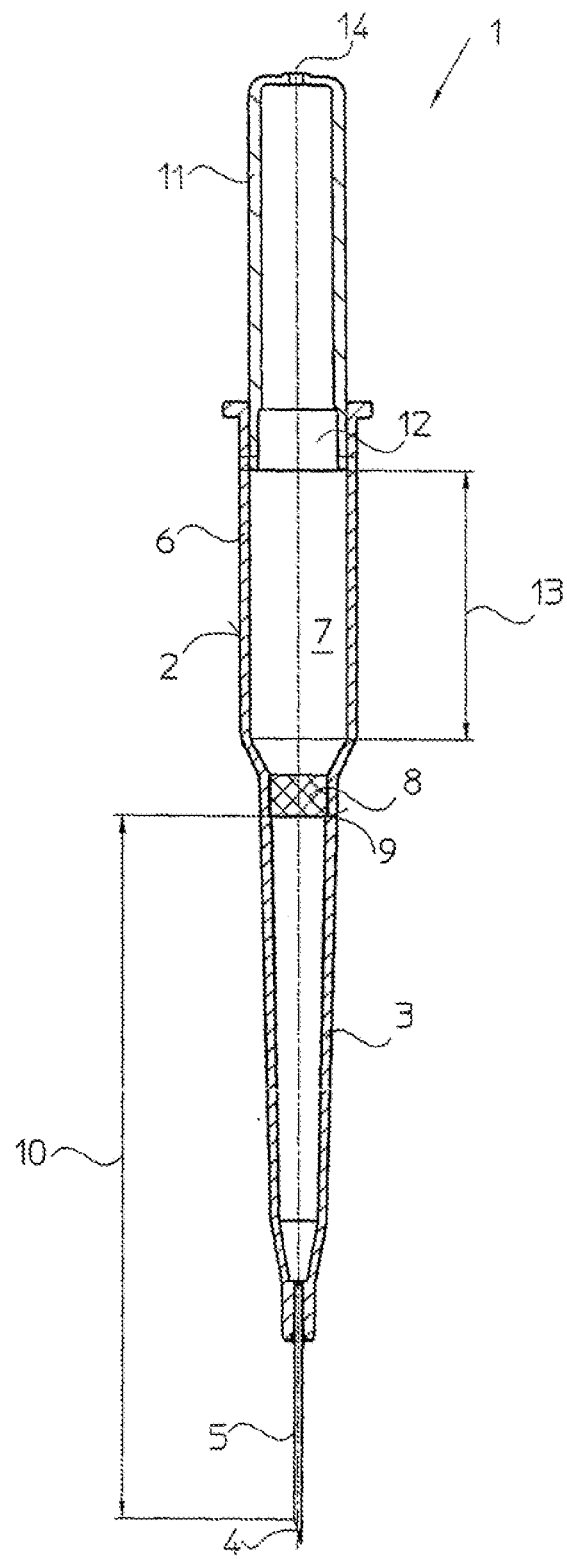

BLOOD-DRAWING DEVICE, IN PARTICULAR FOR INFANTS AND SMALL CHILDREN OR SMALL ANIMALS

CROSS REFERENCE TO RELATED APPLICATIONS

This application is the US national phase of PCT application PCT/DE2005/000737, filed 21 Apr. 2005, published 10 Nov. 2005 as WO2005/104947, and claiming the priority of German patent application 102004021741.6 itself filed 30 Apr. 2004, whose entire disclosures are herewith incorporated by reference.

FIELD OF THE INVENTION

The invention relates to a blood-drawing device, in particular for infants and small children or small animals, comprising a blood-holding receptacle provided on its front end with a needle having a sharpened tip.

BACKGROUND OF THE INVENTION

A blood-drawing device is known from DE 39 32 112 (U.S. Pat. No. 5,165,419), having an outer blood-holding receptacle that is hermetically sealed at its rear end and is sealed at its front end up to the level of a vent port, and that accommodates a concentrically positioned internal specimen tube. The specimen tube is provided on its front end with a needle that may be inserted into the vein of a patient, and at its rear end is in fluid communication with the blood-holding receptacle. The needle is fitted to a holder or Luer fitting that is fixed to a cone for the specimen tube. This blood-drawing device composed of an external blood-holding receptacle and an internal specimen tube is very bulky, and despite use of transparent material for the blood-holding receptacle and the specimen tube is not user-friendly, which complicates observation of the blood flow and makes handling cumbersome. In addition, it is difficult to take defined, small specimen quantities for analytical purposes from the large quantity of blood drawn.

After drawing venous blood, the detachable holder or Luer needle supporting the needle must first be carefully removed and disposed of. This entails the risk of needle sticks from the needle, which in addition is unavoidably wet with blood. The internal, tube- or capillary-like specimen tube is then removed in order to empty the drawn quantity of blood into the external blood-holding receptacle. Blood is likewise unavoidably drawn out when the specimen tube is removed.

Notwithstanding, this known blood-drawing device is not suitable for drawing small quantities of blood, in particular from infants and small children or small animals, on account of their other physiological considerations, in particular the much lower venous pressure. This is because the low blood pressure in these patients is not sufficient for the blood, which initially flows through the cavity of the needle, to flow opposite to the air that is invariably present in the connected specimen tube, causing the blood flow in the needle to cease. Therefore, for drawing blood from infants or the like, only the previously removed Luer needle is used, whose cavity in the insert element receives the drawn quantity of blood. Blood drawing using only the Luer fitting is very difficult and requires an experienced user. Finally, the residual quantity of blood remaining in the Luer fitting relative to the low specimen volume is excessive upon emptying into a specimen vessel, and a defined drawing of a specimen quantity is not possible at all.

The preceding similarly applies when, in particular for avoiding the residual quantity remaining in the Luer fitting, the Luer fitting is removed and then only the needle is employed. The blood specimen can then be emptied directly into a specimen vessel from the open, possibly also curved, rear end of the needle. Since it is very problematic to hold a collection vessel below the open end of the needle to enable reliable collection of the blood specimen, one person holds the patient and performs the puncture operation while another person holds the specimen vessel for receiving the blood.

To improve the drawing of venous blood in infants and is premature babies, nursing infants, and small children, it is known from DE 100 603 02 A1 to equip a hollow needle provided on its distal end with a sharpened tip, with a blood outlet, laterally angled with respect to the longitudinal axis of the hollow needle or needle, at the rear, proximal end thereof. The needle is mounted in a holder so that the grip region behind the blood outlet provides a possibility for handling or guiding. For blood drawing, a vessel that collects the flowing blood is held below the outlet opening of the needle. Compared to conventional injection needles in use, the needle for this blood-drawing device requires no special preparations such as breaking off a Luer cone. However, visual inspection of the quantity of blood to be drawn is inadequate at best, since for these blood-drawing devices of limited size the handle and/or the finger of a person drawing the blood may significantly limit or even completely obstruct the view of the outlet opening. Furthermore, as a result of the laterally angled outlet opening the needle allows optimal blood flow in only one position of use. Aside from the fact that manufacture of a curved, laterally angled needle is complex, there is also the disadvantage that the higher flow resistance in the needle as the result of the curvature hinders the flow of the blood, which in any case is drawn in only a small quantity.

OBJECT OF THE INVENTION

The object of the invention, therefore, is to provide a generic blood-drawing device that does not have the referenced disadvantages, and in particular to improve the user-friendliness and ease of operation and allow the reliable drawing of even small quantities of blood.

SUMMARY OF THE INVENTION

This object is achieved according to the invention by the fact that a porous, air-permeable limiting element that is pressed in in a defined position and that automatically stops the flow of the drawn blood is provided in the blood-holding receptacle, and the rear end of the blood-holding receptacle is sealed by a plunger that may be temporarily vented for drawing blood and that, for delivering the drawn blood to a specimen vessel by means of a stroke guided in a sealed manner in the blood-holding receptacle, empties under pressure at least a partial quantity of the blood confined upstream from the limiting element. This results in a very compact device that does not require special handing of the needle, so that blood flow may be observed without impairment, there are no blood losses, and precisely defined blood drawing and delivery of an exact desired specimen quantity are made possible. The needle may be designed as one piece with the blood-holding receptacle, or may have a detachable design for connection thereto.

The air-permeable limiting element stops further blood collection on first blood contact, i.e. as soon as the specified filling volume is achieved. The limiting element provides an exact volume determination for the blood specimen to be collected, since the limiting element maintains a defined and unchanged position in the blood-holding receptacle, preferably as the result of an internal stop against which the limiting element is inserted and pressed in during manufacture. This is completely different from the purpose of porous filter elements, known as such, provided in pipette tips, for example. In such cases the filter element is intended to prevent contamination of the pipette by aerosols, for example, for which contact with the collected liquid is not desired. In addition, it is not critical for ensuring the functionality of such a pipette tip if a defined filter position is not precisely maintained.

Furthermore, the blood-drawing device according to the invention allows the specified quantity of blood collected in the blood-holding receptacle, including the interior of the needle, to be expelled in the desired amount for analysis, since the quantity of blood may be emptied completely, or alternatively with staged metering, by a plunger stroke. The capability for venting the plunger, for example by means of a plunger retainer that fits loosely in the delivered state of the blood-drawing device and therefore in the blood-drawing or blood-collection position, or by means of a vent port in the plunger, preferably at the upper end thereof, provides the venting required for drawing of the specimen quantity. On the other hand, the required seal between the plunger and the vessel housing for forced emptying is created by pressure accompanied by discontinuation of the provided venting, specifically, when the plunger is moved from the vented, loose starting position into the sealed delivery path, or, for a plunger that is sealed from the outset, when the vent port is closed by a finger.

In one proposal of the invention, the front end of the blood-drawing device containing the needle and the limiting element is designed as a tube. The tube assists in drawing the blood into the collection chamber of the blood-drawing device that is delimited by the filter element.

BRIEF DESCRIPTION OF THE DRAWING

Further features and particulars of the invention result from the claims and the following description of one exemplary embodiment of the invention, illustrated in the single drawing as a general view in a longitudinal section.

SPECIFIC DESCRIPTION

A blood-drawing device 1 illustrated in the FIGURE has a blood-holding receptacle 2 that in the illustrated embodiment has on its front end a frustoconically tapered tube 3 holding a needle 5 that has a sharpened tip 4 and that merges in one piece with a cylindrical section 6 of much greater diameter that adjoins it to the rear. The tube 3 is separated from the chamber 7 of the cylindrical section 6 by a porous limiting element 8 that is pressed against a stop 9 for the blood-holding receptacle in a defined manner, and that precisely defines the collection volume of the tube 3 by virtue of this exact positioning. As soon as the drawn blood reaches the limiting element 8, intake through the needle 5 is stopped. In this way a specimen volume 10 may be determined or specified in a very precise manner. As a result of direct contact of the needle 5 with the front end of the blood-drawing device 1, in this case the tube 3 in the blood-holding receptacle 2, any contour transitions that interfere with blood flow or handling are avoided. Since the blood-drawing device 1 is also self-contained, there is no risk of contamination.

A plunger 11, shown in its starting position for blood collection or drawing, is provided at the end of the blood-holding receptacle 2 opposite the tube 3. For venting during blood drawing, a plunger head 12 that moves forward into the cylindrical section 6 is sealed in the blood-holding receptacle 2 from the outset. The plunger 11 maintains this seal even during movement through its stroke 13 for emptying the collected quantity of blood, to which end a vent port 14, provided for blood drawing in the shown starting position of the plunger 11, at the upper end thereof, is closed by an operator placing a finger thereover during displacement. Alternatively, the plunger head 12 could be provided with a gap facing the inner vessel wall that, as the result of a complementary structural design of the mutually facing walls of the plunger head 12] and inner wall of the cylindrical section 6, closes when the plunger head 12 enters the delivery stroke 13.

For drawing a specimen, the collected quantity of blood defined by the abutment of the limiting element 8 in the tube 3, including the interior of the needle 5, may be expelled by the plunger 12 in a simple manner, preferably as a total metered quantity but also as a partial metered quantity, into a separate specimen vessel (not shown) into which the specimen quantity flows through the needle 5. In this manner it is possible to empty a specimen without residue or losses, which is particularly important when only small amounts of blood are drawn.

The invention claimed is:

1. A blood-drawing device comprising:
a blood-holding receptacle having a front end;
a frustoconically tapered tube of smaller diameter than the receptacle, extending from the front end, and opening rearwardly into the receptacle;
a tubular needle fixed on and projecting forwardly from the tube and having a sharpened front tip;
a porous, air-permeable limiting element engaged in the tube rearward of the needle, the element being of such a porosity that blood cannot flow through the element;
a stop fixing the element in the tube against forward and rearward movement therein; and
a ventable plunger shiftable in the receptacle rearward of the element for pressurizing the receptacle, forcing air therethrough, and expelling blood in the tube through the needle, whereby when the plunger is vented blood can flow through the needle into the tube forward of the element by displacing air rearwardly out of the tube through the element into the receptacle and from the receptacle through the plunger.

2. The blood-drawing device defined in claim 1 wherein the plunger is tubular, fits sealingly in the receptacle, and has a rear end formed with a vent hole blockable by a finger.

3. The blood-drawing device defined in claim 2 wherein the plunger and receptacle are of cylindrical shape.

* * * * *